United States Patent [19]

Gipson

[11] Patent Number: 5,846,746
[45] Date of Patent: Dec. 8, 1998

[54] ANTIBODY TO OCULAR AND VAGINAL SURFACE EPITHELIUM

[75] Inventor: Ilene K. Gipson, Concord, Mass.

[73] Assignee: Schepen's Eye Research Institute, Inc., Boston, Mass.

[21] Appl. No.: 544,755

[22] Filed: Oct. 18, 1995

Related U.S. Application Data

[63] Continuation of Ser. No. 153,817, Nov. 17, 1993, abandoned.

[51] Int. Cl.$^6$ ..................... G01N 33/543; G01N 33/577; C07K 16/28
[52] U.S. Cl. ................... 435/7.21; 435/7.95; 435/70.21; 435/172.2; 435/240.27; 435/975; 436/518; 436/530; 436/548; 530/388.2; 530/391.3; 935/104; 935/110
[58] Field of Search ..................................... 435/7.2, 7.21, 435/7.95, 70.21, 172.2, 240.27, 975; 530/388.2, 391.3; 935/104, 110; 436/518, 530, 548

[56] References Cited

U.S. PATENT DOCUMENTS

| | | |
|---|---|---|
| 4,818,682 | 4/1989 | Linnane . |
| 4,863,854 | 9/1989 | Mattes et al. . |
| 4,939,240 | 7/1990 | Chu et al. . |
| 5,075,219 | 12/1991 | Ceriani et al. . |
| 5,077,220 | 12/1991 | Ceriani et al. . |

OTHER PUBLICATIONS

Dupuy et al, 1990. Characterization of a Monoclonal Antibody Against a Nucin-type Glycoprotein in Human Sweat. Hybridoma 9(6):589–596.
Finstad et al, 1991. Some Monoclonal Antibody Reagents . . . Contain Antibodies to Blood Group A Carbohydrate Determinants . . . J. Histochem and Cytochem 39:1603–1610.
Gooi et al, 1982. Natural Antibodies as Contaminants of Hybridoma Products. Biochem Biophys Res Comm. 106:539–45.
Lloyd, 1987. Blood Group Antigens as Markers for Normal Differentiation and Malignant Change in Human Tissues. AJCP 87: 129–139.
Tisdale et al, 1994. Distribution of a Mucin-like Glycoprotein on Apical Cells and Conjunctiva From Patients With Dry Eye. Invest. Opthalmology and Visual Sci 35:1691 Abstract #2024-11.
Watanabe et al, 1991. Binding Characteristics of a Human Ocular Surface Epithelium Monoclonal Antibody. Invest. Ophthalmology and Visual Sci 32:1073 Abstract #1991-68.
Carlstedt et al., "Mucous glycoproteins: a gel of a problem," Essays Biochem 20:40 (1985).
Carraway et al., "O–glycosylation pathway for mucin–type glycoproteins," BioEssays 10:117 (1989).
Chao et al., "Studies on the isolation and composition of human ocular mucin," Exp. Eye Res. 47:185 (1988).
Devine et al., "Mucins: Structure, function, and associations with malignancy," BioEssays 14:619–625 (1992).
Dilly et al., "Surface changes in the anaesthetic conjunctiva in man, with special reference to the production of mucus from a non–goblet–cell source," Br.J.Ophtalmol. 65:833 (1981).
Feizi et al., "Carbohydrates as antigenic determinants of glycoproteins," Biochem. J. 245:1, (1987).
Friend et al., "Conjunctival goblet cell frequency after alkali injury is not accurately reflected by aqueous tear mucin content," Invest. Ophthalmol. Vis. Sci.. 24:612 (1983).
Gipson et al., "Characteristics of a glycoprotein in the ocular surface glycocalyx," Invest. Ophthalmol. Vis. Sci. 33:218 (1992).
Greiner et al., "Histochemical analysis of secretory vesicles in nongoblet conjunctival epithelial cells," Acta Ophthalmol. 63:89 (1985).
Kaul et al., "Initial characterization of a chlamydial receptor on mammalian cells," FEMS Microbiol. Lett. 57:65 (1989).
Kessing "Mucous gland system of the conjunctiva," Acta Ophthalmol. (Copenh. Suppl. 95:1 (1968).
Kornfeld et al., "Assembly of asparagine–linked oligosaccharides," Annu. Rev. Biochem. 54:631 (1985).
Lamberts "Dry eye and tear deficiency," Int. Ophthalmol. Clin. 23(1):123 (1983).
Lubniewski et al., "Diagnosis and management of dry eye and ocular surface disorders," Corneal Ext. Disease 3:575–594 (1990).
Moore et al, "Human ocular mucus: Chemical studies," Exp. Eye Res. 33:203 (1981).
Nichols et al., "Surface features of the conjunctiva and cornea," Invest. Opthalmol. Vis. Sci. 24:570 (1983).
Nichols et al., "Demonstration of the mucous layers of the tear film by electron microscopy," Invest. Ophthalmol. Vis. Sci. 26:464 (1985).
Oriol et al., "Genetics of ABO, H, Lewis X and related antigens," Vox. Sang. 51:161 (1986).
Versura et al., "Mucus alteration and eye dryness," Acta Ophthalmol. 67:455–464 (1989).
Zhang et al., "Mechanism of C. trachomatis attachment to eukaryotic host cells," Cell 69:861 (1992).
Huang et al., "Development of Monoclonal Antibodies to Rabbit Ocular Mucin," Investigative Ophthalmology and Visual Science, 28:1483–1491 (1987).

*Primary Examiner*—Paula K. Hutzell
*Assistant Examiner*—James L. Grun
*Attorney, Agent, or Firm*—Weingarten, Schurgin. Gagnebin & Hayes LLP

[57] ABSTRACT

A monoclonal antibody has been produced that binds to apical cells of human ocular surface and vaginal epithelia. The antigen recognized by this monoclonal antibody is a mucin-like cell surface glycoprotein. The antibody is of diagnostic use in the evaluation of the ocular surface in dry eye patients, and the antigen has therapeutic potential for use in treatment of dry eye disease. In a comparison of dry eye and normal patients the pattern of antibody binding to dry eye ocular surface epithelia has been shown to differ from the binding pattern seen in normal epithelia.

11 Claims, 3 Drawing Sheets

ANTIBODY TO OCULAR AND VAGINAL SURFACE EPITHELIUM

This application is a continuation of application Ser. No. 08/153,817, filed Nov. 17, 1993, now abandoned.

GOVERNMENT RIGHTS

Part of the work leading to this invention was carried out with United States government funds. Therefore, the U.S. government has certain rights in this invention.

FIELD OF THE INVENTION

This invention relates to a human monoclonal antibody that binds to a specific antigen expressed by epithelial cells, especially ocular and vaginal epithelial cells, and to the use of the monoclonal antibody to diagnose dry eye disorders.

BACKGROUND OF THE INVENTION

The ocular surface epithelium, which covers the conjunctiva and cornea, is made up of three to seven cell layers. The outer layer of apical cells is covered by the tear film, which consists of an outer oily layer, a middle fluid layer and, adjacent to the apical cell membrane, a mucus layer. The spread of mucus over the apical cells is believed to be facilitated by the glycocalyx present on the apical cell membrane (Nichols et al., Invest. Ophthalmol. Vis. Sci. 24:570, 1983). The glycocalyx is a carbohydrate-rich, extrinsic cell surface coat to which the mucus layer loosely binds.

The mucus layer, which stabilizes the liquid tear film and prevents surface drying (Carlstedt et al., Essays Biochem. 20:40, 1985), contains glycoproteins called mucins. Mucins are believed to be secreted onto the ocular surface epithelium by conjunctival goblet cells (Kessing, Acta Ophthalmol. (Copenh) Suppl. 95:1, 1968). Other sources of ocular surface mucins have been suggested, but no data proving production by alternative cell types have been published. Observations that a decrease in goblet cell frequency does not directly correlate with loss of tear mucin content in alkali-burned corneas suggest an alternative source (Friend et al., Invest. Ophthalmol. Vis. Sci. 24:612, 1983). Vesicles containing mucin have been reported to be present in apical cells of conjunctival epithelium in patients with or without contact lenses (Greiner et al., Acta ophthalmol. 63:89, 1985) and in a biopsy of an anesthetic human conjunctiva (Dilly et al., Br. J. Ophthalmol. 65:833, 1981). These studies used toluidine-blue or Alcian-blue PAS stains, which bind highly glycosylated molecules. Thus, a second source of mucin has been proposed (Greiner et al., Acta Ophthalmol. 63:89, 1985), but definitive biochemical identification of mucins produced in these epithelial cells is lacking.

Mucins are highly glycosylated o-linked glycoproteins that are 50–90% (by weight) carbohydrate. Carbohydrate occurs as neutral and acidic oligosaccharides made of varying numbers of monosaccharides in linear and branched sequences. Sugars typically present are N-acetyl glucosamine, N-acetyl galactosamine, galactose, fucose and sialic acid. They are o-glycosidically-linked through N-acetyl galactosamine residues to serine or threonine in the core protein (for review, see Carlstedt et al., Essays Biochem. 20:40, 1985). Compared to N-linked glycoproteins, the biosynthesis of o-linked glycoproteins is simpler in that all sugars are added to the chain by individual transfers from their nucleotide derivatives at sites on the luminal surfaces of organelles, which are primarily Golgi vesicles (for review, see Carraway et al., BioEssays 10:117, 1989).

Some biochemical characterization of purified human ocular surface mucins has been carried out, using mucus threads collected from the nasal canthus (Chao et al., Exp. Eye Res. 47:185, 1988; Moore et al., Exp. Eye Res. 33:203, 1981). Purified mucin has been found to have a minimum molecular weight of 120 kD and to consist of 25–30% protein and 54–55% carbohydrate. Forty-five-49% of hydroxy amino acids in human ocular surface mucins are o-glycosidically linked, as compared with 68% and 62% in bovine and ovine submaxillary mucins, respectively. Despite the characterization studies of ocular mucins, little is known about their source (e.g. goblet cell, "second" mucus source) or about the factors regulating their synthesis.

In addition, little is known about the biochemical properties of the glycocalyx of ocular surface apical cells or its role in the spread of mucus over the apical cells. Electron microscopy shows a filamentous glycocalyx extending from apical membranes, particularly from the tops of microplicae (Nichols et al., Invest. Ophthalmol. Vis. Sci. 24:570, 1983; Nichols et al., Invest. Ophthalmol. Vis. Sci. 26:464, 1985). Most cell surface glycoproteins are molecules in which the oligosaccharides are linked to the protein backbone by the amino acid asparagine. The biosynthetic pathway of these N-linked glycoproteins has been well characterized (Kornfeld et al., Annu. Rev. Biochem. 54:631, 1985). The oligosaccharide chains of these glycoproteins are assembled as lipid intermediates within the endoplasmic reticulum. The intermediates are then attached as an assembled oligosaccharide to an asparagine on the protein backbone. After assembly, trimming or additions of sugars may occur, usually within the Golgi. More specific studies on the biosynthesis and biochemical characteristics of the glycoconjugates on the ocular surface glycocalyx may yield information about the interaction of the glycocalyx and the mucus layer of the tear film.

Abnormalities of the mucus layer of the tear film are one of several causes of dry eye disease (Lubniewski et al., Corneal Ext. Disease 3:575, 1990). Dry eye is a painful condition in which the tear film that normally bathes the surface of the eye is disrupted. In patients with dry eye, dry spots and "filaments" form on the ocular surface. In cross-section the filaments have a PAS-positive central core surrounded by epithelium (Lamberts, Int. Ophthalmol. Clin. 23(1):123, 1983). PAS is a periodic acid Schiff reagent that stains glycoproteins and is routinely used for detecting mucins. The spread of mucus in these patients may be faulty because of a defect in the interaction between the apical cell glycocalyx and the mucus layer or because of a defect in the mucins themselves. It has been reported that the glycosidic content of the mucus produced by goblet cells, as determined by lectin-gold cytochemistry, is altered in dry eye compared to normal patients, while the mucus from vesicles in conjunctival epithelium appears unaffected (Versura et al., Acta Ophthalmol. 67:455, 1989).

Clinical tests for the diagnosis of dry eye disease are Rose bengal staining (Rose bengal is a dye that stains mucus and desiccated epithelial cells), tear break up time or BUT (used to measure tear film stability), and the Shirmer test (used to evaluate tear secretion). These commonly used tests do not reveal the specific cause of dry eye. Conventional non-surgical therapies for dry eye include frequent application of artificial tears.

Definitive biochemical analyses of whether ocular surface mucins are altered in a disease such as dry eye are lacking. Numerous studies to isolate and characterize mucins and cell surface glycoproteins have used monoclonal antibodies as tools (for review, see Feizi et al., Biochem. J. 245:1, 1987), and a rat-specific monoclonal antibody that binds to ocular surface epithelia has been isolated (Gipson et al., Invest. Ophthalmol. Vis. Sci. 33:89, 1992). It would be useful to obtain a human monoclonal antibody against a similar target.

SUMMARY OF THE INVENTION

The invention is derived from the discovery of a monoclonal antibody, H185, that binds to the apical cells of human ocular surface and vaginal epithelia. The antibody does not cross-react with other species. In the course of the production of the antibody, it was discovered that the blood type of the antigenic tissue effected antibody character. The monoclonal antibody isolated recognizes all designated tissues regardless of blood type.

Thus, the invention features, in one aspect, the monoclonal antibody, H185, which is produced by the hybridoma cell line deposited with the American Type Culture Collection (ATCC) as Hybridoma Deposit No. HB11488 and which binds to an epitope on a cell surface glycoprotein antigen expressed by human epithelial cells. Also included within the invention are antibodies that bind specifically to the same human epitope as does the monoclonal antibody H185 and compete with the H185 for binding at that epitope, Fab, F(ab')$_2$, and Fc fragments and conjugates of H185. The invention further includes the hybridoma cell line ATCC No. HB11488, which produces the monoclonal antibody H185.

The monoclonal antibodies, or antibody fragments, of the invention may be conjugated to a label capable of producing a detectable signal such as a radionuclide, an enzyme, a fluorescent agent or a chromophore. Such labeled antibodies or antibody fragments are useful in diagnostic or screening assays.

The monoclonal antibody or antibody fragments of the invention, whether or not conjugated to a label capable of producing a detectable signal, can be used in vitro as screening or diagnostic agents, e.g., in immunohistochemical staining of epithelial cells obtained by filter paper stripping of the ocular surface to detect changes in epithelial cell secretions. For example, in a study of dry eye and normal patients using the monoclonal antibody H185 to examine ocular surface epithelia, antibody binding patterns of the dry eye patients were found to differ from those of the normal patients. In normal epithelium the antibody was bound in a relatively even distribution on the surface cells. In dry eye patients, however, many cells showed no antibody binding; scattered cells that did bind the antibody were round and exhibited intense binding.

The invention also includes using the antibodies of the invention as carriers to target a therapeutic agent, such as an antibiotic, an anti-inflammatory, or an anti-glaucoma or anti-chlamydial agent, to the site of antibody binding, e.g., the ocular or vaginal surface epithelium. In this way, the antibody conjugate can be used to treat a patient suffering from a specific disease condition susceptible to the therapeutic agent. The monoclonal antibodies can also be used to identify a cell surface glycoprotein antigen of the invention, e.g., the H185 antigen, to which the antibodies bind and to identify epitope-containing fragments of the antigen. An epitope-containing fragment of the antigen that is specifically bound by the monoclonal antibody H185 is also included within the invention, as is a therapeutic composition containing such an epitope-containing fragment.

The invention further features a kit for detecting the presence of the antigen of the invention. The kit includes a component for obtaining a sample of epithelial cells from the tissue of interest, e.g., filter paper for filter paper stripping of a sample of ocular surface epithelial cells, and a detectable quantity of the monoclonal antibody or antibody fragment of the invention. The kit can further include a component to disclose the presence of the antibody, i.e., a component including a label capable of producing a detectable signal. In one aspect the discloser is directly conjugated to the monoclonal antibody or antibody fragment. Alternatively, the discloser is a separate entity that is capable of reacting with the antibody after the antibody has been reacted with a tissue sample. Preferably, the detectable signal is visible under a light microscope.

Other features and advantages of the invention will be apparent from the following description of the preferred embodiment thereof and from the claims.

BRIEF DESCRIPTION OF THE DRAWINGS

The file of this patent contains at least one color micrograph. Copies of this patent with color micrographs(s) will be provided by the Patent and Trademark Office upon request and payment of the necessary fee.

FIG. 1A, light micrograph (300 X) of a typical cross-section of human cornea; FIG. 1B, light micrograph (300 X) of binding of monoclonal antibody H185 to cross-sections of human cornea (fluorescence indicates binding to apical cells of the epithelium); FIG. 1C, electron micrograph (21,300 X) of binding of monoclonal antibody H185 to cross-sections of human cornea (electron dense gold particles indicate binding); and FIG. 1D, light micrograph (300 X) of binding of monoclonal antibody H185 to human vaginal epithelial cells obtained by scraping the vaginal wall;

DESCRIPTION OF THE PREFERRED EMBODIMENTS

Monoclonal Antibody Production

Initially, routine methods for monoclonal antibody production and hybridoma screening were used, based in general on the techniques of Kohler and Milstein (Nature 256:495–497, 1975 or Eur. J. Immunol. 6:511–519, 1976). Corneal epithelial cells were obtained from discarded tissue from patients undergoing vitrectomy. No selection criteria for cornea tissues were used. The cells were mixed with RIBI adjuvant (Immunochem. Research, Hamilton, Mont.) and injected into mice. Two booster injections were given, and cell fusion was performed four days after the second boost. Spleen cells from an immunized mouse were mixed with NS-1 myeloma cells (ATCC, Rockville, Md.). The fusion yielded 290 hybridomas, the supernatants of which were screened using cryostat sections of human corneas. Again, no selection criteria were used in obtaining corneas for screening. A hybridoma of interest was selected for cloning. Unexpectedly, the monoclonal antibody produced by this hybridoma did not bind to every human cornea sampled. It was discovered afterwards that it bound to human ocular surface epithelia in blood type A individuals only. Therefore, the first monoclonal antibody isolated was not useful as a universal antibody.

Investigations next centered on finding the cause of this anomaly. Blood group antigens have been described as the major alloantigens of most epithelial cell types in addition to being present on red blood cells (Oriol et al., Vox Sang 51:61, 1986). From the results of the first attempts at isolating a monoclonal antibody to human ocular surface epithelium, it appears that the blood type of ocular antigenic tissue effects antibody character. Therefore, the usual procedures of monoclonal antibody production had to be changed in order to develop a useful monoclonal antibody that would bind to all human ocular surface epithelia regardless of blood type. For the subsequent rounds of hybridoma production, donor eyes of blood type O only were selected and used for immunogen preparation and hybridoma screening, according to the following procedure.

Human limbal and corneal epithelial cells, scraped from eyes of blood type O, were mixed with RIBI adjuvant and injected into mice. Two booster injections were given at three-week intervals. Four days after the last boost, cell fusion was performed. Spleen cells from an immunized mouse were mixed with NS-1 myeloma cells (ATCC, Rockville, Md.) in a ratio of 5:1. The fusion yielded 212 hybridoma cell cultures, the supernatants of which were screened using human blood type O corneas. Nine hybridomas were of interest, and three, including H185, were selected for cloning. H185 was cloned by limiting dilution two times, and subclones were screened by immunofluorescence using human corneas of all blood types. H185 was positive for apical cell binding regardless of blood type.

The isotype of H185 is IgG1.

Tissue Localization of the H185 Antigen

Figure 1A:
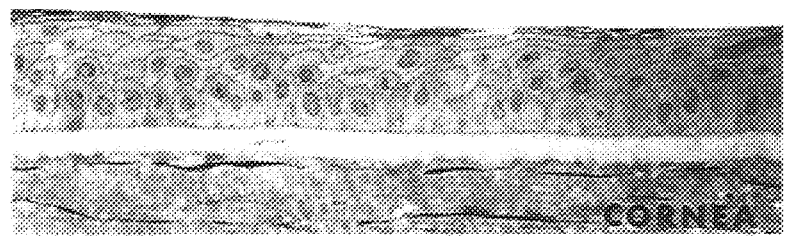
FIGS. 1A–1D show binding of monoclonal antibody H185 of the invention to human cornea and vagina.
Figure 1B:
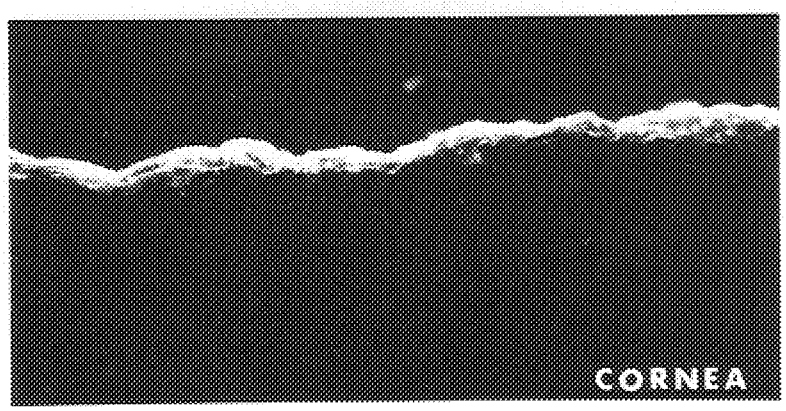

To determine the tissue distribution of the H185 antigen, immunofluorescence studies were carried out by methods previously described (Gipson et al., Invest. Ophthalmol. Vis. Sci. 33:218, 1992). The antigen bound by H185 was localized to the apical cell layers of the corneal epithelium (FIG. 1B). No binding was seen in the basal cell layers or in the stroma or endothelium of the cornea. The antigen was also present in conjunctival, vaginal, tracheal and laryngeal epithelia, and in non-lactating mammary ducts, the eccrine sweat gland and the submucosal gland of the large intestine. The antigen was not present in epidermal, oral mucosal, esophageal, intestinal, liver or bladder epithelia.

To investigate the relationship of the H185 antigen to known mucins, immunofluorescence localization of the only other known epithelial mucin, muc-1 (Devine et al., BioEssays 14:619, 1992) was done, using a commercially available monoclonal antibody (HMFG-1, Biodesign International, Kennebunkport, ME) to muc-1. The localization of muc-1 is different from that of the H185 antigen, indicating that the H185 antigen is not muc-1.

Cellular Localization of the H185 Antigen

Figure 1C:
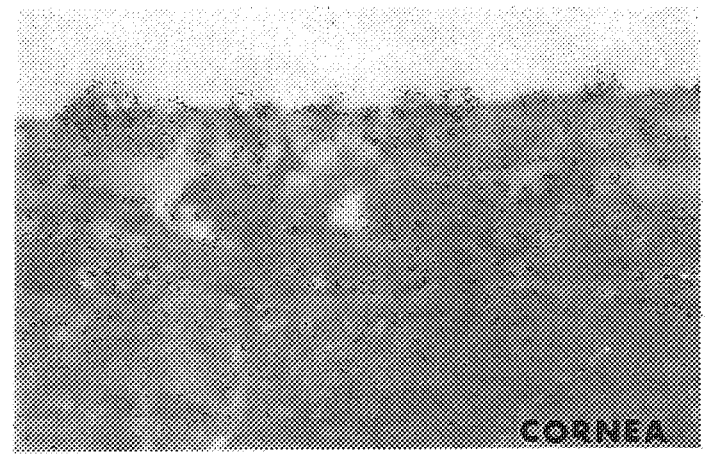
Figure 1D:
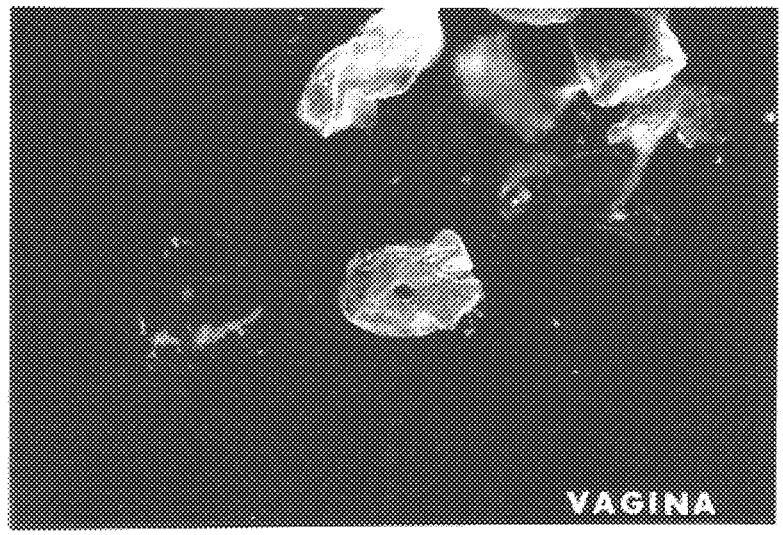

To determine the cellular localization of H185, fixed pieces of human cornea were prepared for immunoelectron microscopy, using methods described previously (Gipson et al., supra). The antigen bound by H185 was localized to the outermost flattened cells of the corneal epithelium, where it borders the tear film (FIG. 1C). Binding appeared to be along the apical cell membranes, especially at the tips of the microplicae or ridges which extend into the tear film. The H185 antigen was also present in subapical cells in small vesicles in the cytoplasm.

Molecular Weight of the H185 Antigen

Figure 2A:
FIG. 2A shows an immunoblot of monoclonal antibody H185 of the invention on human corneal epithelial whole cell extract.

Solubilized corneal epithelia from human eyes were analyzed by sodium dodecyl sulfate-polyacrylamide gel electrophoresis (SDS-PAGE) and immunoblotting, using procedures described previously (Gipson et al., supra). The H185 antigen was detected as a protein just entering a 6% gel. The molecular weight was greater than 205kD (FIG. 2A).

Solubility Properties of the H185 Antigen

Figure 2B:
FIG. 2B shows an immunoblot of monoclonal antibody H185 of the invention on the soluble fraction of human corneal epithelial cell extract.

To investigate the solubility characteristics of the H185 antigen, cultured human corneal epithelial cells were solubilized and centrifuged at 300,000 x g. The supernatant and pellet were separated, the pellet was solubilized, and both were analyzed by SDS-PAGE, followed by immunoblotting with H185. H185-positive bands of equivalent molecular weight were found in both the soluble and membrane-bound fractions. An additional 300,000 x g pellet was resolubilized in a sonicator, and centrifuged again at 300,000 x g. When the supernatant and pellet were tested as above for H185 reactivity, only the pellet was H185 positive. These results indicate that H185 recognizes an antigen that has a soluble component (FIG. 2B).

Unlike the other known epithelial mucin, muc-1, which is known to be a integral membrane protein, the H185 antigen has solubility properties that indicate it is not integral to membranes.

Epitope Characterization and Glycosylation Characteristics of the H185 Antigen Periodate oxidation removes the epitope recognized by H185, indicating that the antigen is a carbohydrate epitope. Periodate oxidation of cryostat sections of human cornea prior to immunofluorescence staining resulted in the absence of H185 binding. H185 binding also was destroyed by periodate oxidation of immunoblots prior to probing with H185.

The glycosylation of the H185 antigen is different from that of the rat-specific ocular surface epithelial antigen R339 (Gipson et al., supra), as shown by three pieces of data. 1) The R339 antigen can be isolated by lectin affinity chromatography using the lectin dolichos biflorus agglutinin (DBA). The H185 antigen does not bind DBA or other lectins tried to date (griffonia (bandeiraea) simplicifolia lectin 1-isolectin B4 (GSL-1B4); ulex europaeus agglutinin I (UEA-I); soybean agglutinin (SBA); griffonia (bandeiraea) simplicifolia lectin II (GSL-II); peanut agglutinin (PNA); and Concanavalin A (Con A)). 2) N-glycanase, an enzyme that removes N-linked carbohydrates on the protein backbone, cleaves sugars from the R339 antigen, changing its molecular weight by SDS-PAGE and immunoblot analysis. N-glycanase treatment has no effect on the H185 antigen. 3) H185 antibody binding to human corneal epithelial cell extracts is destroyed by o-glycanase treatment, indicating that the carbohydrates recognized by H185 are o-linked to the protein core. Cultured human corneal cell extracts were treated first with neuraminidase, an exoglycosidase, then incubated with o-glycanase. The samples were run on 6% SDS-PAGE, followed by immunoblotting with H185. This treatment has no effect on the R339 antigen. These three studies show distinct differences between the H185 and R339 antigens.

Diagnostic and Therapeutic Uses

Both the cellular localization of the H185 antigen, between apical epithelial cells and their mucus coating, and the distribution of the antigen in both ocular surface and vaginal epithelia suggest that the molecule may be of clinical importance. The two clinical problems affecting these epithelial areas are dry eye disease and chlamydial infection.

As indicated above, dry eye describes a variety of ocular surface disorders resulting from tear film, eyelid, conjunctival or corneal abnormalities. Symptoms include dryness, irritation, burning and the sensation of sandy or gritty particles in the eye. Severe cases of dry eye may lead to corneal infections or impairment of vision.

Dry eye is often seen in post-menopausal women. In dry eye disease, dry spots and spots that stain with Rose bengal dye develop on the ocular surface epithelium. It appears that the H185 antigen facilitates the spread of mucus and tear film over the ocular surface and that the dry spots and Rose bengal spots represent a lack of this glycocalyx molecule.

A study of dry eye and normal patients has been carried out, using monoclonal antibody H185 to detect the presence of the H185 antigen in ocular surface epithelia. Localization of the H185 antigen in the ocular surface epithelia of 15 dry eye and 8 normal patients was performed using a filter paper stripping technique. After sterile proparacain hydrochloride was applied to the eye, a sterile strip of pure nitrocellulose (Schleicher & Schuell) was gently placed on the bulbar conjunctive for 5 seconds and removed. The strip was cut in half (one half for test and one for negative control), placed cell side down on gelatin-coated slides and allowed to dry. A drop of ophthalmic antibiotic was placed in the sampled eye to prevent infection. The slides were put into 100% methanol, placed on a shaker for 90 minutes and rinsed in PBS. Immunofluorescence staining was done as described previously, using H185 as the primary antibody and FITC-donkey anti-mouse IgG as the secondary antibody. Filter paper stripping removes the superficial cell layers (top 1–3 layers) of the ocular surface epithelium (the apical-most cells).

Figure 3A:
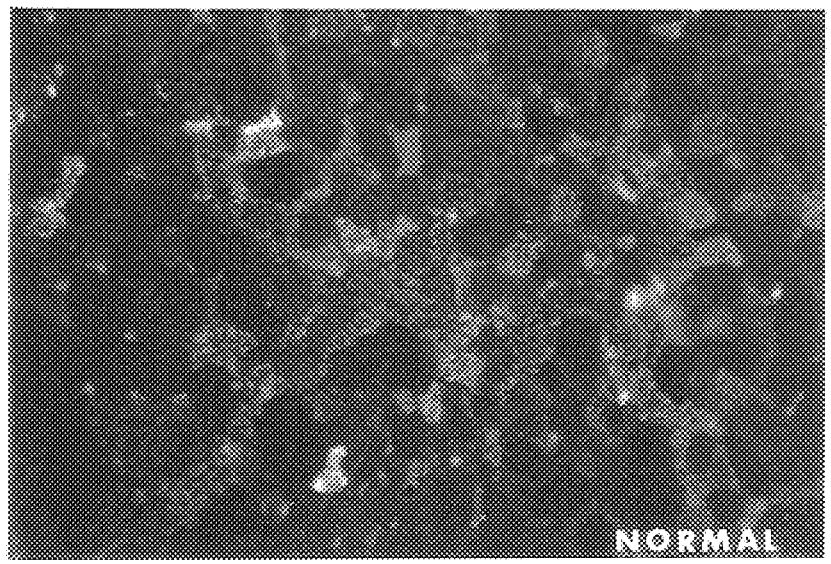
FIGS. 3A–3B show binding of monoclonal antibody H185 of the invention to conjunctival surface of normal (FIG. 3A) and dry eye (FIG. 3B) patients, at a magnification of 300 X.
Figure 3B:
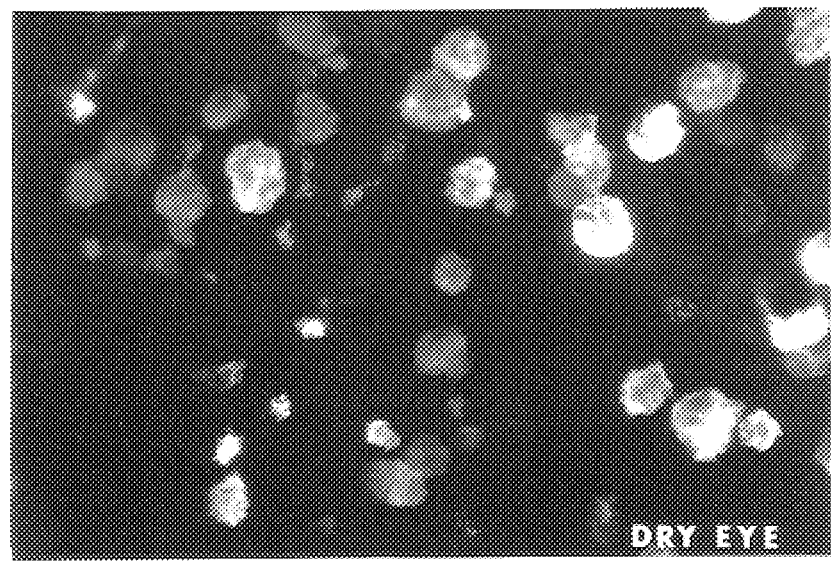

The antibody binding patterns of the dry eye patients differed from those of the normal patients. In normal epithelium the antibody is bound in a relatively even distribution on the surface cells (FIG. 3A). In dry eye patients, many cells show no antibody binding; cells that do bind the antibody are round and bind the antibody intensely (FIG. 3B). Immunoelectron microscopy verifies that epithelial cells in a patient with dry eye contain no H185 antigen and that the intensely binding cells are goblet cells.

The monoclonal antibody H185 will be of diagnostic use in the evaluation of dry eye disorders. There are multiple causes of dry eye, and there is a need for tests that are diagnostically more specific. Commonly used tests for dry eye, such as Rose bengal, tear break up time and Shirmer, do not reveal the specific cause of an individual's dry eye disorder. Even if a tear film abnormality is suspected, the defect could be in either the aqueous, mucus or lipid layer of the tear film. The monoclonal antibody H185 can be used to diagnose abnormalities specifically in the mucus layer of the tear film. The use of H185 to detect the H185 antigen on filter paper stripping samples of ocular surface epithelium is a noninvasive test that is easy to perform. Unlike Rose bengal, which can be irritating or painful, filter paper stripping can be carried out with no discomfort to the patient.

A simple kit for clinical use to detect the H185 antigen on epithelial cells, e.g., ocular surface epithelium, would include a component for removing a sample of epithelial cells, e.g., filter paper for filter paper stripping of samples, and a detectable quantity of monoclonal antibody or antibody fragments of the invention. The kit could also include an agent serving as a discloser of the presence of the antibody or antibody fragment. The discloser could be a label capable of producing a detectable signal which was conjugated to the antibody or antibody fragment. Alternatively, the discloser could be a separate entity, e.g., a secondary antibody capable of reacting with the monoclonal antibody or antibody fragment of the invention and carrying a detectable signal. Preferably, the detectable signal would be visible under a light microscope, e.g., a chromophore.

The characterization of the H185 antigen will yield information regarding construction of synthetic products for use as artificial tear substitutes. Thus, the H185 antigen, or portions thereof, has potential therapeutic uses in the treatment of dry eye disease. For example, the antigen or fragment would be useful in therapy for the treatment of post-menopausal epithelial drying.

The H185 antigen is also of potential therapeutic use in the treatment of chlamydial infections. The distribution of the H185 antigen in the ocular surface and vagina is the same as that of the sites of chlamydial infection. As the characteristics of Chlamydia receptors are not yet known (Kaul et al., FEMS Microbiol. Lett. 57:65, 1989; Zhang et al., Cell 69:861, 1992), the H185 antigen could be a Chlamydia receptor. Therefore, characterization of the H185 antigen can lead to the development of better agents to prevent or treat chlamydial infection. For example, the isolated H185 antigen or portions thereof can be used as competitive inhibitors to prevent pathogen adherence, for prophylactic or therapeutic purposes.

Deposits

The following samples were deposited on Nov. 11, 1993, with the American Type Culture Collection (ATCC), 12301 Parklawn Drive, Rockville, Md. 20852.

| Deposit | ATCC Accession No. |
| --- | --- |
| Hybridoma H185 | HB 11488 |

Applicant's assignee, The Schepens Eye Research Institute, Inc. represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC §122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A monoclonal antibody or monoclonal antibody fragment selected from the group consisting of a monoclonal antibody produced by the hybridoma cell line deposited with the American Type Culture Collection (ATCC) as ATCC No. HB 11488, and Fab, F(ab')$_2$ and Fc fragments of the monoclonal antibody produced by hybridoma cell line ATCC No. HB 11488.

2. The monoclonal antibody or monoclonal antibody fragment of claim 1 conjugated to a detectable label.

3. The monoclonal antibody or monoclonal antibody fragment of claim 2, wherein the label is selected from the group consisting of a radionuclide, an enzyme, a fluorescent agent and a chromophore.

4. A hybridoma cell line deposited with the American Type Culture Collection as ATCC No. HB 11488.

5. A method of diagnosing a change in the extent or pattern of H185 antigen distribution in ocular epithelial tissue in a human patient, said method comprising removing a sample of cells or secretions from ocular epithelial tissue in said patient;

reacting said tissue sample with a detectable amount of the monoclonal antibody or monoclonal antibody fragment of claim 1;

detecting said monoclonal antibody or monoclonal antibody fragment specifically bound to said tissue sample; and comparing the extent or pattern of binding of said monoclonal antibody or monoclonal antibody fragment to said tissue sample to the extent or pattern of binding of said monoclonal antibody or monoclonal antibody fragment to a reference ocular epithelial tissue sample.

6. A method of diagnosing a change in the extent or pattern of H185 antigen distribution in ocular epithelial tissue in a human patient, said method comprising removing a sample of cells or secretions from ocular epithelial tissue in said patient;

reacting said tissue sample with a detectable amount of the monoclonal antibody or monoclonal antibody fragment of claim 2;

detecting said monoclonal antibody or monoclonal antibody fragment specifically bound to said tissue sample; and comparing the extent or pattern of binding of said monoclonal antibody or monoclonal antibody fragment to said tissue sample to the extent or pattern of binding of said monoclonal antibody or monoclonal antibody fragment to a reference ocular epithelial tissue sample.

7. A kit for detecting the presence of H185 antigen in human epithelial tissue, said antigen being capable of specifically binding to the monoclonal antibody or monoclonal antibody fragment of claim 1, said kit comprising a component for obtaining a sample of human epithelial tissue; and a detectable quantity of the monoclonal antibody or monoclonal antibody fragment of claim 1.

8. The kit of claim 7 further comprising a component to disclose the presence of said monoclonal antibody or monoclonal antibody fragment, said component comprising a detectable label.

9. The kit of claim 8 wherein said discloser is conjugated to said monoclonal antibody or monoclonal antibody fragment.

10. The kit of claim 8 wherein said discloser is separate from said monoclonal antibody or monoclonal antibody fragment and, in use specifically binds to said monoclonal antibody or monoclonal antibody fragment.

11. A method of identifying a cell surface glycoprotein antigen from human epithelial tissue that is bound specifically by a monoclonal antibody produced by hybridoma cell line ATCC No. HB 11488, said method comprising providing a sample of human epithelial tissue;

reacting said sample with a detectable amount of a monoclonal antibody produced by hybridoma cell line ATCC No. HB 11488;

detecting any binding of said monoclonal antibody to an antigen in said sample that is specifically bound by said monoclonal antibody; and identifying an antigen in said sample that is bound specifically by said monoclonal antibody.

* * * * *